(12) United States Patent
Bhavsar et al.

(10) Patent No.: US 12,409,156 B2
(45) Date of Patent: Sep. 9, 2025

(54) STABLE AQUEOUS HYDROXYCARBAMIDE SOLUTION

(71) Applicant: Nova Bio-Pharma Product Development LTD, Wigston (GB)

(72) Inventors: Khunal Bhavsar, Wigston (GB); Michael Edge, Wigston (GB); Claire Hodkinson, Wigston (GB); Kelly Grant, Wigston (GB); Hussain Mulla, Wigston (GB); Peter White, Wigston (GB)

(73) Assignee: Nova Bio-Pharma Product Development LTD, Wigston (GB)

( * ) Notice: Subject to any disclaimer, the term of this patent is extended or adjusted under 35 U.S.C. 154(b) by 951 days.

(21) Appl. No.: 17/055,332

(22) PCT Filed: May 17, 2019

(86) PCT No.: PCT/GB2019/051362
§ 371 (c)(1),
(2) Date: Nov. 13, 2020

(87) PCT Pub. No.: WO2019/220134
PCT Pub. Date: Nov. 21, 2019

(65) Prior Publication Data
US 2021/0220299 A1   Jul. 22, 2021

(30) Foreign Application Priority Data
May 17, 2018   (GB) ..................................... 1808013

(51) Int. Cl.
| | |
|---|---|
| *A61K 31/17* | (2006.01) |
| *A61K 9/08* | (2006.01) |
| *A61K 47/02* | (2006.01) |
| *A61K 47/14* | (2017.01) |
| *A61K 47/26* | (2006.01) |
| *A61K 47/36* | (2006.01) |

(52) U.S. Cl.
CPC ................ *A61K 31/17* (2013.01); *A61K 9/08* (2013.01); *A61K 47/02* (2013.01); *A61K 47/14* (2013.01); *A61K 47/26* (2013.01); *A61K 47/36* (2013.01)

(58) Field of Classification Search
CPC .......... A61K 31/17; A61K 9/08; A61K 47/02; A61K 47/14; A61K 47/26; A61K 47/36
See application file for complete search history.

(56) References Cited

U.S. PATENT DOCUMENTS 3,119,866 A   1/1964   Wisogle

FOREIGN PATENT DOCUMENTS

WO   WO 00/51620 A1   9/2000

OTHER PUBLICATIONS

Remington's pharmaceutical sciences, 17th ed. Edited by Alfonso R. Gennaro. Mack Publishing Co., 20th and Northampton Streets, Easton, PA 18042. (Year: 1985).*
Remington's pharmaceutical sciences, pp. 1492-1503, 17th ed. Edited by Alfonso R. Gennaro. Mack Publishing Co., 20th and Northampton Streets, Easton, PA 18042. (Year: 1985).*
Heeney, Matthew M. et al; Chemical and Functional Analysis of Hydroxyurea Oral Solutions; Journal of Pediatric Hematology/Oncology; Mar. 2004; vol. 26, No. 3, Mar. 2004 (Mar. 2004); Lippincott Williams & Wilkins, Wolters Kluwer Health; Philadelphia, Pennsylvania.

* cited by examiner

*Primary Examiner* — Adam C Milligan
*Assistant Examiner* — Jed A Kucharczk
(74) *Attorney, Agent, or Firm* — Dority & Manning, P.A.

(57) ABSTRACT

The present invention provides a stable aqueous hydroxycarbamide solution comprising: hydroxycarbamide; a pH adjuster being sodium hydroxide, potassium hydroxide, sodium bicarbonate, and sodium carbonate, or a mixture of one or more of these substances; and optionally a preservative being a base of methyl hydroxybenzoate and/or ethyl hydroxybenzoate; wherein: the solution is controlled to have a pH of between 6.1 and 7.1. The solution of the present invention is beneficial as compared to solutions according to the prior art in that it can be safely stored at ambient temperatures for prolonged periods of time without significant degradation.

20 Claims, No Drawings

STABLE AQUEOUS HYDROXYCARBAMIDE SOLUTION

RELATED APPLICATION

This application claims priority of PCT Application No. PCT/GB2019/051362, filed on May 17, 2019, and United Kingdom Patent Application No. 180813.5, filed on May 17, 2018, both of which are incorporated by reference in their entirety herein.

FIELD OF INVENTION

The present invention provides a stable aqueous hydroxycarbamide (also known as hydroxyurea) solution that is useful for the treatment of sickle cell disease, particularly in children and in patients suffering from dysphagia.

BACKGROUND TO THE INVENTION

Hydroxycarbamide:

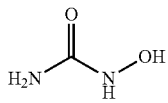

is a compound that is approved in the EU for the treatment of symptomatic sickle cell syndrome and in the US for symptomatic sickle cell anaemia in adults and children over the age of 2 years. Presently, there is no approved disease modifying agent appropriate for children under 2 years of age. There is significant clinical data showing that hydroxycarbamide is effective in the treatment of all aspects of sickle cell disease (SCD), reducing acute complications, whilst increasing the quality of life. A growing body of data also documents improved organ function and prolonged survival.

Recent clinical data, which evaluated hydroxycarbamide as an oral solution for treatment of children under 2 years of age indicates that hydroxycarbamide treatment should be extended to asymptomatic children with SCD, including infants from the age of 9 months.

Hydroxycarbamide is currently available as several brand name products including Hydrea®, Droxia®, Siklos® as well as FDA approved generic products. All currently availably Hydroxycarbamide products are only available as an oral capsule or tablet formulation with doses of 100 mg, 200 mg, 300 mg, 400 mg, 500 mg, and 1000 mg strengths. There is no currently approved stable solution of hydroxycarbamide.

The lack of availability of a stable solution of hydroxycarbamide is problematic for a large proportion of the SCD population. In particular, it can be difficult to individualise doses using solid capsules or tablets. This is a particular issue in SCD, where the maximum tolerated dose (MTD) can be highly variable, ranging from 15 to 35 mg/kg/day. This broad range in MTD is at least partially due to the substantial inter-patient variability in hydroxycarbamide pharmacokinetics and pharmacodynamics and prevents the ability to use a standard effective dose for all SCD patients. In adult patients hydroxycarbamide exposure varies approximately five-fold for a given dosing regime, whereas in paediatric patients differences in exposure can vary two to three-fold at the same mg/kg dose. As a result, dosages of hydroxycarbamide need to be individualised to achieve the best clinical outcomes. The best way to administer a precisely individualised dose of any drug is through the use of an oral liquid solution.

In addition, patients with dysphagia have difficulty taking current solid forms of hydroxycarbamide. There is a similar problem with paediatric patients under the age of 6, who may refuse or find it difficult to take hydroxycarbamide in solid form due to difficulty swallowing and/or lack of palatability.

In light of the above there is a need for a stable oral solution of hydroxycarbamide. Any such oral solution should have a shelf life of at least 12 months within a defined temperature range (generally 2° C. to 8° C. and/or <25° C.). In order for a hydroxycarbamide formulation to be considered acceptably stable by pharmaceutical regulators, any degradant formed on storage must not exceed 0.15% w/v unless its molecular composition has been positively identified, and it has been demonstrated to be safe through toxicity or clinical studies. In addition, any such solution should preferably be palatable so that it can be used in paediatric patients.

Previous studies have indicated that chemical stability of hydroxycarbamide is challenging as it is a highly soluble compound that has been reported as being unstable in an aqueous environment (El-Yazigi et al, Pharmaceutical Research, Vol. 9, No. 1, 1992). The degradation pathways are not clearly defined in existing literature but hydrolysis has been considered to be the most likely pathway (Alvarez and Slade, Pharmaceutical Research, Vol. 9, No. 11, 1992; McLoughline et al, J. Pharm. Pharmacol. 1998, 50: 127-132). There have been suggestions that relatively stable hydroxycarbamide solutions may be able to be formulated (Heeney et al, J. Pediatr Hematol Oncol; Vol 26, Number 3, March 2004; Kabiche et al, Int J Pharm Comp; Vol 21, Number 2, 2017). However, such formulations had proposed shelf-lives <4 months, the assay data presented was highly variable, and no attempt had been made to characterise the impurities or their safety. On all of these criteria, previously published formulations would not be considered stable by pharmaceutical regulators, and would not therefore be viable as commercial pharmaceutical products.

U.S. Pat. No. 3,119,866 relates to "stabilized hydroxyurea" and discloses a method of producing a dry stable composition that is a mixture of hydroxycarbamide and a substance that buffers an aqueous solution in the pH range of about 5.5 to about 6.5. The suitable buffer substances that are disclosed include potassium citrate, disodium hydrogen citrate, and mixtures of compounds such as citric acid and disodium phosphate and potassium acid phosphate and disodium phosphate. The dry composition is prepared by dissolving the buffer and the hydroxycarbamide in water and then evaporating off the water. The hydroxycarbamide is not maintained in aqueous solution for any length of time during the method disclosed.

Importantly, the composition disclosed in U.S. Pat. No. 3,119,866 is only stable as a dry composition, after evaporation of all water. The aqueous solution that is prepared as an intermediate step to obtaining the dry composition has been found to only be stable at room temperature (25°) for approximately 36 hours. After this time unacceptable levels of degradation products are present in the aqueous solution. As a result, it has previously been considered that the use of pH buffers such as potassium citrate and citric acid/sodium citrate to stabilise solutions of hydroxycarbamide is not effective. At temperatures between 2° C. and 8° C., the applicant has discovered that the main degradation product of hydroxycarbamide solutions is carbamoyloxyurea. The International Conference on Harmonisation of Technical Requirements for Registration of Pharmaceuticals for Human Use (ICH) stipulates that the maximum allowable limit for any degradant in a formulation should not exceed 0.15% w/v, at therapeutic doses of hydroxycarbamide in the treatment of sickle cell disease. However, the present applicant has conducted rat toxicology studies that show that carbamoyloxyurea does not pose a risk over and above hydroxycarbamide (hydroxyurea). As a result, the European Medicines Agency has now accepted that carbamoyloxyurea contents of up to 0.5% w/v are acceptable.

In light of the above, in the context of the present invention, stable formulations may have up to 0.5% w/v carbamoyloxyurea after storage for the relevant period within the necessary temperature range. A formulation will not be deemed to be stable if the carbamoyloxyurea content exceeds 0.5% w/v within one month when stored at the necessary temperature range. That is, in order to be stable the carbamoyloxyurea content cannot exceed 0.5% w/v within one month and the levels of other unacceptable degradation products must not exceed acceptable limits within the same time period. Generally, solutions will need to be stored at both 2° C. to 8° C. and 25° C. for periods of up to 1 month.

At temperature ranges other than 2° C. to 8° C., the degradation profile of hydroxycarbamide solutions differs from that at standard room temperature. In particular, at standard room temperature conditions other degradation products are produced. As some storage at room temperature is generally required, in order for a solution to be considered to be stable it must be able to be stored at room temperature for at least one month, even if it is generally intended to be stored at other temperature ranges e.g. 2° C. to 8° C.

SUMMARY OF INVENTION

The present invention provides a stable aqueous hydroxycarbamide solution comprising:
hydroxycarbamide; and
a pH adjuster being one of sodium hydroxide, potassium hydroxide, sodium bicarbonate, and sodium carbonate, or a mixture of one or more of these substances;
wherein:
the solution is controlled to have a pH of between 6.1 and 7.1.

The pH adjuster of the present invention is one of sodium hydroxide, potassium hydroxide, sodium bicarbonate, and sodium carbonate, or a mixture of one or more of these substances. The pH adjuster is used to control the pH of the aqueous solution to be within the desired range of 6.1 to 7.1. The amount of pH adjuster in a solution of the present invention will be an amount that properly controls the pH of the solution depending on the hydroxycarbamide content of the solution and the specific pH adjuster used. It is anticipated that the skilled person will be able to determine an appropriate amount of pH adjuster for any particular embodiment of the present invention. As described below, embodiments of the invention wherein the pH adjuster is sodium hydroxide have been tested and found to be stable. As the other listed pH adjusters operate in substantially the same manner it is anticipated that the other pH adjusters are also suitable. The use of pH adjuster has been found to be particularly advantageous as compared to pH buffers used in the prior art because, as set out below, it acts to maintain the stability of the aqueous solution at 25° C. for periods of up to one month.

The solution of the present application has been found to be stable for extended periods, providing excellent stability over a period of at least 12 months when stored at between 2° and 8° C. The solution of the present invention has excellent stability over a period of at least one month when stored at 25° C./60% RH. The solution remains stable with the addition of flavouring, allowing for more palatable solutions that are particularly suitable for use by paediatric patients. The solution is stable regardless of the presence or absence of suitable flavouring. The solution may be used with paediatric patients with the presence or absence of flavouring.

In some embodiments of the invention it is not necessary for the solution to comprise a preservative. A preservative may not be required because hydroxycarbamide has significant anti-microbial activity and can therefore act as a preservative itself. The mechanism of hydroxycarbamide's preservative action is described in "Hydroxyurea Induces Hydroxyl Radical-Mediated Cell Death in *Escherichia coli*." Bryan Davies et al. Molecular Cell, Dec. 11, 2009. It is anticipated that in embodiments of the present invention with relatively high hydroxycarbamide contents, for example 5% w/v or higher, then a preservative may not be required.

In some embodiments of the invention the solution may further comprise a preservative. In such embodiments the preservative may comprise methyl, ethyl, butyl, or propyl hydroxybenzoate bases or salts or any other equivalent compound apparent to the person skilled in the art. In a particularly preferred embodiment of the invention the preservative may be methyl hydroxybenzoate base. Any suitable amount of preservative may be used. Most preferably the amount of preservative is from 0.01% w/v to 0.1% w/v.

In order to improve mouth feel and palatability of the solution of the present invention the solution may further comprise a viscosity modifying agent. Any suitable viscosity modifier apparent to the person skilled in the art that does not adversely affect the properties of the solution may be used. Xanthan gum has been investigated (see below) and has been found to be a suitable viscosity modifying agent. Solutions with 0.4% w/v of xanthan gum and 10% w/v hydroxycarbamide have been found to be suitable. Solutions with a ratio of 1:25 xanthan gum to hydroxycarbamide are considered to be suitable. However, other ratios of xanthan gum: hydroxycarbamide may also be suitable, for example ratios of 1:10 to 1:50 are considered likely to be acceptable.

In order to improve palatability of the solution of the present invention the solution may further comprise a sweetener. Any suitable sweetener may be used. Suitable sweeteners include, but are not limited to, sucralose, aspartame, acesulfame k and equivalents. A 0.25% w/v concentration of sucralose has been found to be suitable. Other concentrations of sucralose may also be suitable, for example concentrations of 0.1% w/v to 0.5% w/v are considered likely to be suitable.

In order to improve palatability of the solution of the present invention the solution may further comprise a flavouring agent. Suitable flavouring agents include but are not limited to standard strawberry, grape, or apple flavoured flavouring agents as provided by Firmenich. In particular, strawberry flavour 501099A, apple flavour 501137 TP0551, and grape flavour 501417C are suitable flavouring agents.

The solution of the present invention may contain any suitable amount of hydroxycarbamide. In embodiments the amount of hydroxycarbamide may be from 5% w/v to 15% w/v, from 9% w/v to 11% w/v, or 10% w/v.

In order to maximise stability it may be preferable that the pH of the solution of the present invention is controlled to be from 6.1 to 7.1., or from 6.5 to 6.7. The target pH of the solution may be 6.6. Generally, controlling the solution to have a target pH of 6.6 will result in the solution having a pH from 6.5 to 6.7. However, controlling the pH to be from 6.1 to 7.1 is considered to provide acceptable stability to the solution.

Further features of the invention will be apparent from the following description setting out the development of the invention from the technical problem of obtaining a stable aqueous solution of hydroxycarbamide.

The solution of the present invention is of particular use in the treatment of sickle cell disease, particularly in paediatric patients and patients with dysphagia. The solution of the present invention also allows individualised doses to be administered more accurately than with previous solid dosage forms of hydroxycarbamide.

The solution of the present invention may be used in a method for the treatment of sickle cell disease characterised in that the solution can be stored at a temperature between 2° C. and 8° C. for at least twelve months before administration. Furthermore, the stable solution of the present invention may be used for treatment of SCD, even after storing at ambient temperatures for periods of up to 1 month, to allow for unintended excursions in storage temperature. That is, the solution of the present invention is stable at ambient temperatures for periods of up to 1 month. The solution of the present invention is stable at temperatures between 2° C. and 8° C. for periods of up to 18 months. In particular, carbamoyloxyurea levels in the solution of the present invention remain below 0.5% w/v when the solution is stored under these conditions.

DEVELOPMENT OF INVENTION

The solution of the present invention was formulated in the following manner.

Initial Formulation

As set out above in the background section, hydrolysis was considered to be the most likely degradation pathway of hydroxycarbamide. Therefore, when developing the present invention pH was considered to be a critical parameter of the solution. Initial formulation stability was investigated at four different pHs: 3.3, 5.2, 7.0 and 8.0. In addition the stability of an unapproved, extemporaneously compounded hydroxycarbamide formulation was studied, which showed the pH drifted significantly from the initial pH. As a consequence, various buffering systems were investigated.

Two main degradation peaks were identified during formulation development stability studies:

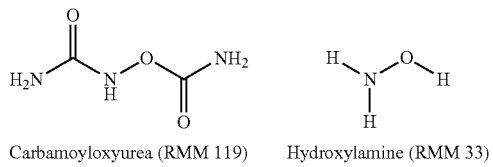

Carbamoyloxyurea (RMM 119)   Hydroxylamine (RMM 33)

Hydroxylamine is a listed related substance in the BP monograph for hydroxycarbamide capsules and has a limit of not greater than 1.0% w/v.

Carbamoyloxyurea was identified using LC-MS.

Stability studies were performed at ICH conditions of 5° C., 25° C./60% RH and 40° C./75% RH.

The pH study demonstrated that samples at pH 7.0 and 8.0 had lower levels of degradation compared to pH 3.0 and pH 5.0. In addition, degradation was significantly reduced for samples stored at 5° C. across all pH ranges tested. At accelerated conditions of 40° C./75% RH, significant degradation and loss in assay was observed. Hence, all subsequent testing was conducted at 5° C. and 25° C./60% RH. Longer term stability studies have shown that the degradants produced at 25° C./60% RH differ from those seen at 5° C. and the relative ratios of the main degradants are also different.

A citric acid/sodium phosphate buffer and a sodium phosphate/sodium phosphate buffer were investigated. These two buffering systems were studied at two concentrations over the pH range of 6.0 to 8.0. In addition the target pH for the concept formulations was 7.2. These excipients were chosen based on the Target Product Profile (TPP) and previous experience with an unapproved, extemporaneously compounded hydroxycarbamide product but also to ensure product performance, conformance and patient compliance.

Samples were stored at 5° C. and 25° C./60% RH and after two weeks, the data demonstrated that the addition of the sodium phosphate/sodium phosphate buffer was detrimental to the stability of hydroxycarbamide. The use of this buffer system was therefore abandoned at this stage.

Batches containing higher concentrations of citric acid/sodium phosphate buffer maintained the product pH more effectively. In addition, after 4 weeks storage at 5° C., these samples showed lower levels of degradation.

Batches prepared with xanthan gum, sucralose and black cherry flavour (Firmenich code 501534 TP0504) at pH 7.2 demonstrated similar trends with one exception; a colour change was observed. After 4 weeks storage the appearance of the batches changed from white to off-white to pink-brown. This was considered to be due to the addition of either xanthan gum, sucralose, or the black cherry flavour.

Second Formulations

Based on the results from the pH and buffer system studies set out above, two batches of solution were manufactured with a target pH of 7.2 One batch was manufactured using a citric acid/sodium citrate buffer at high concentration. The second batch was a non-buffered formulation with a pH adjustment using citric acid.

The formulations are summarised as follows:

TABLE 1

| Raw Material | Concentration (% w/v) | |
| --- | --- | --- |
| Target pH | 7.20 | 7.20 |
| Hydroxycarbamide | 10 | 10 |
| Sodium methyl hydroxybenzoate | 0.1145 | 0.1145 |
| Sodium ethyl hydroxybenzoate | 0.0566 | 0.0566 |
| Potassium sorbate | 0.1 | 0.1 |
| Citric Acid | ~0.045* | qs* |
| Tri-sodium citrate dihydrate | qs* | — |
| Black cherry flavour | 0.4 | 0.4 |
| Sucralose | 0.1 | 0.1 |
| Xanthan Gum | 0.3 | 0.3 |
| Sterile Purified Water | to 100% | to 100% |

*as required to achieve target pH

Following storage for 13 weeks at 5° C., the hydroxylamine content for both batches was <0.1% w/v. It was anticipated that the levels of hydroxylamine would be less than 1.0% w/v (BP Monograph limit) after 52 weeks at 5° C.

The carbamoyloxyurea content for the batch containing buffer was 0.17% w/v after 13 weeks storage at 5° C. whereas the content for the pH adjusted batch was 0.22% w/v. However, storage of the batch containing buffer at 25° C./60% RH showed high level of unknown and unacceptable degradants as well as urea, and it was therefore considered that the addition of the citric acid buffer system offered no overall improvement in stability.

During execution of the above study, a colour change was observed after 48 hours storage at ambient temperatures. Both formulations changed from an off white translucent solution to pink-brown colour. Subsequent storage at ambient temperatures resulted in a further change to a pale yellow colour.

An excipient compatibility study was carried out to investigate the colour change. The results showed that the change was due to an unexpected interaction of the black cherry flavour and the sodium salts of preservatives which only occurred in the presence of hydroxycarbamide.

Third Formulations

Further studies were undertaken to optimise the formulation to reduce the levels of carbamoyloxyurea formed during storage. The following parameters were investigated:
  pH (ranging from 4 to 8)
  use of Ethylenediaminetetraacetic acid (EDTA), a chelating agent;
  preservative system; sodium salts of methyl hydroxybenzoate and ethyl hydroxybenzoate vs the bases of methyl hydroxybenzoate and ethyl hydroxybenzoate;
  influence of degassing the formulation (to remove dissolved oxygen) and packing under nitrogen.

The formulations investigated at pH 6.0 showed slightly lower amounts of carbamoyloxyurea being formed during storage.

The data generated from these studies showed that the use of EDTA, degassing the formulation or packing under nitrogen had no significant impact on reducing the amount of carbamoyloxyurea formed.

The use of methyl hydroxybenzoate and ethyl hydroxybenzoate bases as preservatives resulted in a very slight reduction in the levels of carbamoyloxyurea formed in comparison with the sodium salts. In parallel to this work, a preservative efficacy study was performed to investigate the effectiveness of the preservative system. The study demonstrated that hydroxycarbamide drug substance has a high level of antimicrobial activity, and was able to inhibit the growth of six organisms tested. Based on this data, the preservative system was modified to contain only methyl hydroxybenzoate base.

During execution of these formulation optimisation studies, an unknown hydroxycarbamide related substance was detected which exceeded 0.2% w/v during storage at 5° C. for 1 week. The unknown degradant was found to be due to an unexpected interaction of the black cherry flavour with the hydroxycarbamide. As a consequence, alternative flavours, strawberry (Firmenich code 501099A), grape (Firmenich code 501417C) and apple (501137 TP0551), were investigated. The strawberry flavour was preferred, with an improved taste profile compared to grape and apple flavours. However, there were no adverse interactions between the grape and apple flavours and the hydroxycarbamide, and these flavours therefore are considered to be suitable with the present invention.

Sodium hydroxide was selected as the pH adjuster of the formulation as it is suitable for use with methyl hydroxybenzoate base.

Target pH

Three levels of xanthan gum were investigated at 0.40% w/v, 0.50% w/v and 0.60% w/v. The formulations were investigated with and without the use of sodium hydroxide for pH adjustment to assess the impact of sodium hydroxide on stability. The 4 weeks stability data did not demonstrate any difference in the degradation profile with respect to addition of sodium hydroxide or change in the xanthan gum levels at 5° C. The use of sodium hydroxide was found to improve stability at 25° C. The formulation containing 0.40% w/v xanthan gum was selected for further optimisation. A batch with the formulation detailed as follows was prepared:

TABLE 2

| Raw Materials | % w/v |
| --- | --- |
| Target pH | 6.2 |
| Hydroxycarbamide (% w/v) | 10 |
| Methyl hydroxybenzoate (% w/v) | 0.05 |
| Sucralose (% w/v) | 0.1 |
| Strawberry flavour (% v/v) | 0.05 |
| Xanthan gum (% w/v) | 0.3 |
| 0.1M Sodium Hydroxide (% v/v) | 3.625 |
| Sterile water for irrigation (% w/v) | to 100 |

This storage of this batch was then investigated at storage conditions of 5° C. and 25° C./60% RH for periods up to 8 weeks with the results as follows:

TABLE 3

| Time point | Storage Condition | HU Content mg/mL | Related Substances % | | | | |
| --- | --- | --- | --- | --- | --- | --- | --- |
| | | | RRT 0.44 | RRT 0.49 | RRT 0.69 | RRT 0.87 | RRT 1.18 |
| Initial | | 101.5 | <0.05 | <0.05 | <0.05 | ND | <0.05 |
| 1 week | 5° C. | 100.9 | <0.05 | ND | <0.05 | ND | <0.05 |
| 2 weeks | 5° C. | 102.0 | <0.05 | <0.05 | <0.05 | ND | <0.05 |
| 16 days | 25° C./60% RH | 100.9 | 0.13 | <0.05 | <0.05 | ND | 0.18 |
| 4 weeks | 5° C. | 100.6 | <0.05 | <0.05 | <0.05 | ND | 0.05 |
| | 25° C./60% RH | 99.5 | 0.12 | 0.05 | <0.05 | ND | 0.21 |
| 8 weeks | 5° C. | 100.4 | <0.05 | <0.05 | <0.05 | ND | 0.07 |
| | 25° C./60% RH | 99.5 | 0.08 | 0.05 | <0.05 | ND | 0.27 |

At a target pH of 6.2 in the samples stored at 25° C./60% RH a peak at RRT 0.44 of an unknown degradant was found. It was considered likely that this peak would also appear in the samples stored at 5° C. over longer time periods.

In order to avoid this peak, a second batch having a target pH of 6.6 with the following formulation was produced:

TABLE 4

| Raw Materials | % w/v |
| --- | --- |
| Target pH | 6.6 |
| Hydroxycarbamide (% w/v) | 10 |
| Methyl hydroxybenzoate (% w/v) | 0.05 |
| Sucralose (% w/v) | 0.2 |
| Strawberry flavour (% v/v) | 0.1 |
| Xanthan gum (% w/v) | 0.4 |
| 1M Sodium Hydroxide (% v/v) | 0.67 |
| Sterile water for irrigation (% w/v) | to 100 |

This storage of this batch was then investigated at storage conditions of 5° C. and 25° C./60% RH for periods up to 8 weeks with the results as follows:

TABLE 5

| Time point | Storage Condition | Assay HU Content mg/mL | Related Substances area % | | |
|---|---|---|---|---|---|
| | | | RRT 0.49 | RRT 1.18 | Others |
| Initial | | 98.7 | ND | ND | ND |
| 2 weeks | 5° C. | 99.0 | ND | <0.05 | <0.05 |
| | 25° C./60% RH | 97.9 | 0.05 | 0.23 | <0.05 |
| 4 weeks | 5° C. | 99.1 | <0.05 | 0.05 | <0.05 |
| | 25° C./60% RH | 97.7 | 0.05 | 0.26 | <0.05 |
| 8 weeks | 5° C. | 99.0 | <0.05 | 0.11 | <0.05 |
| | 25° C./60% RH | 97.5 | <0.05 | 0.41 | 0.11 |

The storage of this batch did not produce the same peak of unknown degradant when stored at either 5° C. or 25° C./60% RH for periods up to 8 weeks. As a result, a target pH of 6.6 was preferred. A target pH of 6.6 generally maintains the actual pH of the solution between about 6.5 and 6.7.

It is noted that the batch with a target pH of 6.6 produced higher levels of carbamoyloxyurea (RRT1.18) when stored at 25° C./60% RH, as compared to the batch with a target pH of 6.2. However, the levels of carbamoyloxyurea remained well within the acceptable limit of 0.5% w/v within the relevant time periods.

The levels of sucralose and strawberry flavour were increased to 0.20% w/v and 0.10% v/v, respectively, to improve palatability.

Final Formulation

Two laboratory-scale batches (1.2 L) of the formulation detailed as follows were manufactured with the addition of excipients and API following different sequences. This formulation is the same as the previous small-scale batch described immediately above.

TABLE 6

| Raw material | % w/v |
|---|---|
| Target pH | 6.6 |
| Hydroxycarbamide | 10% |
| Methyl Hydroxybenzoate | 0.05% |
| Sucralose | 0.25% |
| Strawberry Flavour | 0.1%* |
| 1M NaOH solution | ~0.7%* |
| Xanthan Gum | 0.4% |
| Sterile water for irrigation | to 100% |

*quantity in % v/v

These formulations were determined to be stable, palatable, and suitable for clinical use, with minimal impact on product stability from the order of addition. In particular, samples from the batches were stored for up to 2 months at 25° C./60% RH and up to 18 months at 5° C. and the carbamoyloxyurea and degradant content was tested at intervals. The results of these tests are shown in the tables below:

TABLE 7

| Time point | Storage condition | Assay: Hydroxycarbamide content (mg/mL) | | | |
|---|---|---|---|---|---|
| | | Batch 1 | Batch 2 | Batch 3 | Batch 4 |
| Initial | | 99.8 | 101.3 | 101.3 | 100.9 |
| 0.5 months | 5° C. | 100.9 | 101.2 | 100.5 | 100.7 |
| | 25° C./60% RH | 99.9 | 100.3 | 99.8 | 99.8 |
| 1 month | 5° C. | 99.9 | 100.0 | 100.1 | 100.6 |
| | 25° C./60% RH | 98.8 | 99.3 | 99.0 | 99.6 |
| 2 months | 5° C. | 100.3 | 101.2 | 100.5 | 99.9 |
| | 25° C./60% RH | 98.9 | 99.9 | 99.3 | 99.1 |
| 3 months | 5° C. | 100.2 | 101.3 | 101.2 | 100.2 |
| 6 months | 5° C. | 99.9 | 101.0 | 100.5 | 100.4 |
| 9 months | 5° C. | 100.1 | 100.8 | 100.7 | 99.8 |
| 12 months | 5° C. | 100.5 | 100.7 | 100.3 | 99.8 |
| 15 months | 5° C. | 99.9 | 100.0 | 99.6 | 98.7 |
| 18 months | 5° C. | 99.3 | 100.0 | 99.7 | TBC |

TABLE 8

| Time point | Storage condition | Carbamoyloxyurea content (% relative to nominal HC content) | | | |
|---|---|---|---|---|---|
| | | Batch 1 | Batch 2 | Batch 3 | Batch 4 |
| Initial | | <0.05 | <0.05 | <0.05 | <0.05 |
| 0.5 months | 5° C. | <0.05 | <0.05 | <0.05 | 0.06 |
| | 25° C./60% RH | 0.21 | 0.21 | 0.21 | 0.25 |
| 1 month | 5° C. | 0.08 | 0.05 | <0.05 | 0.06 |
| | 25° C./60% RH | 0.27 | 0.24 | 0.25 | 0.27 |
| 2 months | 5° C. | 0.09 | 0.11 | 0.11 | 0.09 |
| | 25° C./60% RH | 0.29 | 0.28 | 0.28 | 0.29 |
| 3 months | 5° C. | 0.13 | 0.10 | 0.10 | 0.14 |
| 6 months | 5° C. | 0.16 | 0.20 | 0.18 | 0.21 |
| 9 months | 5° C. | 0.24 | 0.22 | 0.21 | 0.22 |
| 12 months | 5° C. | 0.27 | 0.22 | 0.22 | 0.24 |
| 15 months | 5° C. | 0.26 | 0.27 | 0.28 | 0.26 |
| 18 months | 5° C. | 0.27 | TBC | TBC | TBC |

TABLE 9

| Time point | Storage condition | Unknown degradant (% relative to nominal HC content) | | | |
|---|---|---|---|---|---|
| | | Batch 1 | Batch 2 | Batch 3 | Batch 4 |
| Initial | | ND | ND | ND | ND |
| 0.5 months | 5° C. | ND | ND | ND | ND |
| | 25° C./60% RH | <0.05 | ND | ND | <0.05 |
| 1 month | 5° C. | ND | ND | ND | ND |
| | 25° C./60% RH | 0.06 | <0.05 | 0.07 | 0.08 |
| 2 months | 5° C. | ND | ND | ND | ND |
| | 25° C./60% RH | 0.17 | 0.13 | 0.13 | 0.22 |
| 3 months | 5° C. | ND | ND | ND | ND |
| 6 months | 5° C. | ND | ND | ND | ND |
| 9 months | 5° C. | ND | ND | ND | ND |
| 12 months | 5° C. | ND | ND | ND | ND |
| 15 months | 5° C. | ND | ND | ND | ND |
| 18 months | 5° C. | ND | ND | ND | ND |

ND = Not Detected
TBC = To Be Confirmed
Hydroxylamine is < 0.1% w/v for all storage conditions and batches The batches were found to be stable at 5° C. for at least 12 months and stable at 25° C./60% RH for at least two months.

Although sodium hydroxide was initially selected as the pH adjuster due to its suitability for use with methyl hydroxybenzoate base, the relatively small amounts of methyl hydroxybenzoate base in the solution and the excellent stability of the solution at both 5° C. and 25° C. indicate that the use of sodium hydroxide as the pH adjuster would provide stability to the solution even in the absence of methyl hydroxybenzoate base. Due to the very slight preservative effect of methyl hydroxybenzoate base (see above) it is anticipated that methyl hydroxybenzoate base could be removed from the final formulation without adverse effect.

What is claimed is:

1. A stable aqueous hydroxycarbamide solution comprising:
   an aqueous solution comprising a hydroxycarbamide, wherein, after the aqueous solution is stored for four weeks at a temperature of 25° C. and 60% RH, the aqueous solution comprises less than 0.5% w/v of carbamoyloxyurea, less than 0.1% w/v of hydroxylamine, and has an initial pH of between 6.5 and 6.7.

2. A stable aqueous hydroxycarbamide solution according to claim 1, further comprising a preservative comprising a methyl hydroxybenzoate or an ethyl hydroxybenzoate.

3. A stable aqueous hydroxycarbamide solution according to claim 1 further comprising a viscosity modifying agent.

4. A stable aqueous hydroxycarbamide solution according to claim 3, wherein the viscosity modifying agent is xanthan gum.

5. A stable aqueous hydroxycarbamide solution according to claim 1, further comprising a sweetener.

6. A stable aqueous hydroxycarbamide solution according to claim 5, wherein the sweetener is sucralose, aspartame, or acesulfame K.

7. A stable aqueous hydroxycarbamide solution according to claim 1, further comprising a flavouring agent.

8. A stable aqueous hydroxycarbamide solution according to claim 1, wherein the hydroxycarbamide content is from 5% w/v to 15% w/v.

9. A stable aqueous hydroxycarbamide solution according to claim 8, wherein the hydroxycarbamide content is from 9% w/v to 11% w/v.

10. A stable aqueous hydroxycarbamide solution according to claim 9, wherein the aqueous solution has a concentration of the hydroxycarbamide of 10% w/v.

11. A stable aqueous hydroxycarbamide solution according to claim 1, wherein the aqueous solution has a pH of 6.6 after the aqueous solution is stored for four weeks at a temperature of 25° C. and 60% RH.

12. A stable aqueous hydroxycarbamide solution according to claim 2, wherein the aqueous solution has a concentration of the preservative of from 0.01% w/v to 0.1% w/v.

13. A stable aqueous hydroxycarbamide solution according to claim 1 comprising:
   a preservative comprising a methyl hydroxybenzoate and/or an ethyl hydroxybenzoate;
   a viscosity modifying agent;
   a sweetener; and
   a flavouring agent.

14. A stable aqueous hydroxycarbamide solution according to claim 1 for use in the treatment of sickle cell disease.

15. A stable aqueous hydroxycarbamide solution comprising:
   a hydroxycarbamide;
   a pH adjuster, wherein the pH adjuster is sodium hydroxide, potassium hydroxide, sodium bicarbonate, sodium carbonate, or a mixture thereof, and wherein the aqueous hydroxycarbamide solution has a pH of between 6.5 and 6.7.

16. A stable aqueous hydroxycarbamide solution according to claim 15, further comprising a preservative comprising a methyl hydroxybenzoate or an ethyl hydroxybenzoate.

17. A stable aqueous hydroxycarbamide solution according to claim 15 for use in the treatment of sickle cell disease.

18. A stable aqueous hydroxycarbamide solution comprising:
   an aqueous solution comprising a hydroxycarbamide;
   a preservative, wherein the preservative comprises a methyl hydroxybenzoate or an ethyl hydroxybenzoate, and wherein, after the aqueous solution is stored for four weeks at a temperature of 25° C. and 60% RH, the aqueous solution comprises less than 0.5% w/v of carbamoyloxyurea, less than 0.1% w/v of hydroxylamine, and has a pH of between 6.5 and 6.7.

19. A stable aqueous hydroxycarbamide solution according to claim 18, wherein the aqueous solution has a pH of 6.6 after the aqueous solution is stored for four weeks at a temperature of 25° C. and a relative humidity of 60% RH.

20. A stable aqueous hydroxycarbamide solution comprising:
   an aqueous solution comprising a hydroxycarbamide, wherein, after the aqueous solution is stored for two years at a temperature of 5° C. and 60% RH, the aqueous solution comprises less than 0.5% w/v of carbamoyloxyurea, less than 0.1% w/v of hydroxylamine, and has an initial pH of between 6.5 and 6.7.

* * * * *